(12) United States Patent
Combrowski et al.

(10) Patent No.: US 9,675,344 B2
(45) Date of Patent: Jun. 13, 2017

(54) SURGICAL INSTRUMENT

(75) Inventors: Zbigniew Combrowski, Tuttlingen (DE); Christel Paroth, Tuttlingen (DE); Alexander Henninger, Muhlheim (DE)

(73) Assignee: Z-Medical GmbH & Co. KG, Tuttlingen (DE)

( * ) Notice: Subject to any disclaimer, the term of this patent is extended or adjusted under 35 U.S.C. 154(b) by 566 days.

(21) Appl. No.: 13/345,006

(22) Filed: Jan. 6, 2012

(65) Prior Publication Data
US 2012/0228355 A1 Sep. 13, 2012

(30) Foreign Application Priority Data

Jan. 7, 2011 (DE) .................. 10 2011 000 058
Jan. 5, 2012 (DE) .................. 10 2012 100 086

(51) Int. Cl.
*A61B 17/04* (2006.01)
*A61B 17/10* (2006.01)
(Continued)

(52) U.S. Cl.
CPC ...... *A61B 17/0642* (2013.01); *A61B 17/0401* (2013.01); *A61B 17/1285* (2013.01); *A61F 2/4455* (2013.01); *A61F 2/4611* (2013.01); *A61B 17/0682* (2013.01); *A61B 17/105* (2013.01); *A61B 17/808* (2013.01); *A61B 17/809* (2013.01); *A61B 2017/00526* (2013.01); *A61B 2017/0409* (2013.01); *A61B 2017/0424* (2013.01); *A61B 2017/0641* (2013.01); *A61B 2017/0646* (2013.01); *A61B 2017/0648* (2013.01); *A61B 2090/037* (2016.02); *A61F 2/30734* (2013.01); *A61F 2002/30136* (2013.01); *A61F 2002/30347* (2013.01); *A61F 2002/30464* (2013.01); *A61F 2002/30515* (2013.01); *A61F 2002/30556* (2013.01); *A61F 2002/30561* (2013.01); *A61F 2002/30576* (2013.01); *A61F 2002/30579* (2013.01); *A61F 2002/30616* (2013.01); *A61F 2002/4475* (2013.01)

(58) Field of Classification Search
CPC ............ A61B 17/068; A61B 17/07292; A61B 2017/0409
USPC .......................................... 227/175.1–182.1
See application file for complete search history.

(56) References Cited

U.S. PATENT DOCUMENTS 975,235 A * 11/1910 Hansen ............... F16B 15/0015
411/476
1,756,670 A * 4/1930 Treat ............................ 606/119
(Continued)

FOREIGN PATENT DOCUMENTS

DE 19859952 A1 2/2000
EP 1552794 A2 7/2005
(Continued)

OTHER PUBLICATIONS

European Patent Office, European Search Report issued in corresponding European patent application No. EP 2474271. Date of Mailing: Jun. 10, 2013.

*Primary Examiner* — Robert Long
(74) *Attorney, Agent, or Firm* — Fishman Stewart PLLC

(57) ABSTRACT

A surgical instrument includes an implant, a grip, and a pre-set breaking point connecting the implant and the grip. The implant has a joining profile.

22 Claims, 37 Drawing Sheets

(51) Int. Cl.

| | |
|---|---|
| *A61B 17/064* | (2006.01) |
| *A61B 17/128* | (2006.01) |
| *A61F 2/44* | (2006.01) |
| *A61F 2/46* | (2006.01) |
| *A61B 17/068* | (2006.01) |
| *A61B 17/80* | (2006.01) |
| *A61B 17/00* | (2006.01) |
| *A61F 2/30* | (2006.01) |
| *A61B 90/00* | (2016.01) |

(56) References Cited

U.S. PATENT DOCUMENTS

| | | | | |
|---|---|---|---|---|
| 3,744,495 | A * | 7/1973 | Johnson | 606/142 |
| 4,278,091 | A * | 7/1981 | Borzone | 606/75 |
| 4,531,522 | A * | 7/1985 | Bedi et al. | 606/220 |
| 4,532,927 | A * | 8/1985 | Miksza, Jr. | 606/220 |
| 4,548,202 | A * | 10/1985 | Duncan | 606/220 |
| 4,573,469 | A * | 3/1986 | Golden et al. | 606/220 |
| 4,627,437 | A * | 12/1986 | Bedi et al. | 606/220 |
| 4,655,222 | A * | 4/1987 | Florez | A61L 31/10 |
| | | | | 411/920 |
| 5,093,558 | A * | 3/1992 | Blystone | H05B 3/32 |
| | | | | 174/158 R |
| 5,209,756 | A * | 5/1993 | Seedhom et al. | 606/151 |
| 5,222,963 | A * | 6/1993 | Brinkerhoff | A61B 17/11 |
| | | | | 227/179.1 |
| 5,282,829 | A * | 2/1994 | Hermes | 606/219 |
| 5,342,396 | A * | 8/1994 | Cook | 606/219 |
| 5,439,479 | A * | 8/1995 | Shichman et al. | 606/220 |
| 5,509,920 | A * | 4/1996 | Phillips et al. | 606/157 |
| 5,620,289 | A * | 4/1997 | Curry | F16B 1/0071 |
| | | | | 411/444 |
| 5,620,452 | A * | 4/1997 | Yoon | 606/151 |
| 5,667,527 | A * | 9/1997 | Cook | 606/219 |
| 5,827,298 | A * | 10/1998 | Hart et al. | 606/139 |
| 5,902,310 | A * | 5/1999 | Foerster | A61B 17/0644 |
| | | | | 606/142 |
| 5,976,159 | A * | 11/1999 | Bolduc | A61B 17/064 |
| | | | | 606/104 |
| 6,391,038 | B2 * | 5/2002 | Vargas | 227/175.1 |
| 6,406,241 | B1 * | 6/2002 | Lorincz | F16B 15/02 |
| | | | | 411/439 |
| 6,419,682 | B1 * | 7/2002 | Appleby | A61B 17/1222 |
| | | | | 206/339 |
| 6,723,099 | B1 | 4/2004 | Goshert | |
| 6,779,959 | B1 * | 8/2004 | Yang | B25C 1/184 |
| | | | | 206/347 |
| 7,111,768 | B2 * | 9/2006 | Cummins | A61B 17/0644 |
| | | | | 227/175.1 |
| 7,497,865 | B2 * | 3/2009 | Willis | A61B 17/11 |
| | | | | 227/175.1 |
| 7,794,475 | B2 * | 9/2010 | Hess | A61B 17/064 |
| | | | | 227/175.1 |
| 8,261,958 | B1 * | 9/2012 | Knodel | A61B 17/064 |
| | | | | 227/176.1 |
| 8,303,228 | B2 * | 11/2012 | Gosis | F16B 19/14 |
| | | | | 411/451.3 |
| 8,403,956 | B1 * | 3/2013 | Thompson | A61B 17/072 |
| | | | | 227/175.1 |
| 8,453,904 | B2 * | 6/2013 | Eskaros | A61B 17/072 |
| | | | | 227/175.1 |
| 8,454,289 | B2 * | 6/2013 | Frantin | F16B 15/0015 |
| | | | | 411/457 |
| 8,469,253 | B1 * | 6/2013 | Knodel | A61B 17/068 |
| | | | | 227/175.1 |
| 8,475,491 | B2 * | 7/2013 | Milo | A61B 17/0644 |
| | | | | 606/213 |
| 8,631,992 | B1 * | 1/2014 | Hausen | A61B 17/0644 |
| | | | | 227/175.1 |
| 9,155,536 | B1 * | 10/2015 | Hausen | A61B 17/068 |
| 2004/0073222 | A1 | 4/2004 | Koseki | 606/75 |
| 2005/0033329 | A1 * | 2/2005 | Bombard | A61B 17/1152 |
| | | | | 606/153 |
| 2005/0075657 | A1 * | 4/2005 | Bombard | A61B 17/1152 |
| | | | | 606/153 |
| 2005/0131428 | A1 * | 6/2005 | Bombard | A61B 17/1152 |
| | | | | 606/139 |
| 2005/0267530 | A1 * | 12/2005 | Cummins | 606/219 |
| 2006/0015144 | A1 * | 1/2006 | Burbank et al. | 606/219 |
| 2006/0039779 | A1 * | 2/2006 | Ringl | 411/457 |
| 2007/0180664 | A1 * | 8/2007 | Perry | F16L 3/04 |
| | | | | 24/115 R |
| 2008/0063491 | A1 * | 3/2008 | Ringl, Jr. | F16B 15/0015 |
| | | | | 411/476 |
| 2008/0172088 | A1 * | 7/2008 | Smith et al. | 606/219 |
| 2008/0173692 | A1 * | 7/2008 | Spurchise | A61B 17/0057 |
| | | | | 227/175.1 |
| 2008/0232929 | A1 * | 9/2008 | Jackson | F16B 15/0015 |
| | | | | 411/476 |
| 2009/0065552 | A1 * | 3/2009 | Knodel | A61B 17/072 |
| | | | | 227/180.1 |
| 2009/0254090 | A1 | 10/2009 | Lizee | |
| 2009/0277948 | A1 * | 11/2009 | Beardsley | A61B 17/0644 |
| | | | | 227/178.1 |
| 2010/0155453 | A1 * | 6/2010 | Bombard et al. | 227/176.1 |
| 2010/0241165 | A1 * | 9/2010 | Konieczynski | A61B 17/7071 |
| | | | | 606/248 |
| 2010/0256675 | A1 * | 10/2010 | Romans | A61B 17/0644 |
| | | | | 606/219 |
| 2010/0280621 | A1 | 11/2010 | Adamo | |
| 2011/0052346 | A1 * | 3/2011 | Frantin | F16B 15/0015 |
| | | | | 411/476 |
| 2011/0112513 | A1 * | 5/2011 | Hester | A61B 17/06166 |
| | | | | 604/514 |
| 2012/0046692 | A1 * | 2/2012 | Smith et al. | 606/219 |
| 2014/0114411 | A1 * | 4/2014 | Baird | A61F 2/0811 |
| | | | | 623/13.14 |
| 2014/0175153 | A1 * | 6/2014 | Manoux | A61B 17/068 |
| | | | | 227/176.1 |

FOREIGN PATENT DOCUMENTS

| | | |
|---|---|---|
| EP | 1882451 A2 | 1/2008 |
| EP | 2106754 A1 | 10/2009 |
| FR | 2731610 A1 | 9/1996 |
| WO | 03030746 A1 | 4/2003 |
| WO | 2004004578 A1 | 1/2004 |
| WO | 2006074414 A2 | 7/2006 |
| WO | 2010127390 A1 | 11/2010 |
| WO | 2012140218 A1 | 10/2012 |

* cited by examiner

SURGICAL INSTRUMENT

CROSS-REFERENCE TO RELATED APPLICATIONS

This application claims the benefit of priority to German Application Nos. 10201100058.5, filed Jan. 7, 2011 and German Application No. 102012100086.7, filed Jan. 5, 2012, both of which are fully incorporated herein by reference as though fully set forth herein.

TECHNICAL FIELD

The invention relates to a surgical instrument as per the features of the preamble of Claim 1, as well as a positioning instrument for the surgical instrument and a drilling template for the surgical instrument

STATE OF THE ART

Staples or clamps are used for joining bone parts, for instance in the hand and foot surgery after Weil, Scarf, Austin, Chevron and Cheil and many other OP applications. The clamps serve the purpose of fixing and/or compression of bone parts and remain inside the body in most cases. Coincidentally, these staples and/or clamps are very small implants and are difficult to hold because of their shape. With positioning instruments as per the state of the art, clamps and/or staples are very time consuming to fix. Another problem with implanting of staples and/or clamps is that normally a drilling is made before positioning the clamp. The drilled bone holes are very difficult to find after removing the drill. From the state of the art drilling templates are well known, nevertheless these cannot be applied in combination with staples.

DESCRIPTION OF THE INVENTION

The objective of the invention is to design a surgical instrument in such a way that the disadvantages mentioned above are removed or at least minimized. Additionally a drilling template and a positioning instrument are to be created for improved implanting of joining profiles or staples.

SOLVING THE PROBLEM

The features of the characterizing part of the Claim 1 lead to solving the problem.

With a surgical instrument with an implant and a grip, the implant and the grip are joined through a pre-set breaking point. Preferably, the implant has a joining profile. The joining profiles are, for instance, screws, braces, cages, staples and/or clamps.

In typical embodiments, the surgical instrument comprises a guiding pipe. Preferably, the guiding pipe presents a diameter smaller than or equal to 4 mm. Especially, the a cannula is preferred s guiding pipe.

As joining profile, different forms come into consideration. As far as possible, in lateral view all the U-profiles, C-profiles, semi-profile or three-fourths profile or pitch circle profile, as well as the implants described as clamps or staples fall under this.

In typical embodiment, the implant is a staple. Staples are suitable for fixing of bone parts and/or soft tissues and/or ligaments and/or sinews.

The term "staple" is applied in German also in the medical technique as technical term for joining profile. Both terms are applied in the present application with same meaning.

Joining profiles with more brackets, for example, 4, 6, 10 limbs/webs which could have shapes like star, honeycomb structure, net structure in preferred forms and not only flat but also in shapes adjusted to suit the bone surfaces and comprise a type of quarter, half, three-quarters or preferred shells which are stamped, pressed in the bones through integrated drilling and fixing templates.

As the joining profiles are very small, these are difficult to grasp and to handle. As the grip part is good to handle in comparison with the joining profile, the implant can be advantageously handled comfortably in to insert, hold, take out, rotated and/or moved by using the grip. If the implant and/or the joining profile is partly implanted, the grip can be separated from the implant and/or the joining profile without using any other tool at the pre-set break point.

The grip can comprise of many parts, for example, it can be of two-parts, in the process, the second grip part that is not connected with the joining profile also has a pre-set break point to the grip that is connected with joining profile, can be broken.

After breaking the second part of the grip, this forms a so-to-say detachable drilling template for the limb of the joining profile, and/or fixing drills and/or guiding areas and/or guiding nuts for guiding the joining profile with the placement of the joining profile in the bones.

In an especially preferred form, the surgical instrument comprises of many pre-set break points. As a result there is advantage that the grip part and the joining profile can be joined together in better way. Another advantage is that between the preset break point preferably recesses are provided. Preferably, these recesses are suitable for insertion of a placement instrument described later.

Joining profile, so staples can also be created from a material that can be implanted and reabsorbed.

Advantageously, the surgical instrument is a single part, for instance, made of a titanium plate or a sheet. Preferred manufacturing process are laser cutting, wire eroding, stamping, bending or shape cutting processes like, milling, cutting, possibly staples made of implantable, absorbable materials or plastics. This is advantageous that the pre-set break point can be prepared very accurately. This is important in order to ensure a breaking of the pre-set breaking point by effecting a definite force and torque. Another advantage of the so-called manufacturing process is that the surgical instrument can be prepared with implant in cost-effective manner.

In typical embodiments, the joining profile and/or the staple comprise a titanium wire. This gives the advantage that the joining profile can be created in a cost-effective manner.

In particular, the pre-set breakpoint and/or the multiple pre-set breakpoints is preferably arranged on the joining profile in such a way that they are arranged in a depression of the joining profile and a burr-free breaking is possible, and the burr lies deeper than the surface of an joining profile. This results in an advantage that the joining profile as well as a possible burr of the pre-set breakpoint does not lead to irritation of the tissue, skin or bones.

In typical embodiment, the joining profile presents a first limb. Preferably, the joining profile presents a second limb. In an especially preferred embodiment, the joining profile presents a suitable web that joints the first and second limb.

Joining profiles with still more limbs/legs, e.g. 4, 6, 10 limbs/legs/webs which could have shapes like star, honeycomb structure, net structure in preferred forms and not only flat but also in shapes adjusted to suit the bone surfaces and comprise a type of quarter, half, three-quarters or preferred shells which are stamped, pressed in the bones through integrated drilling and fixing templates.

In typical embodiments, the first and the second limb of the joining profile runs parallel to each other. In these cases, the limb and the web join in an angle between 120° and 15°. Preferred embodiments of the joining profile are the so-called 90° joining profile and the so-called 26° joining profile. With 90° joining profile, the web and a limb join in a 90° angle. With 26° joining profile the parallel limb elbows by 26° to the web.

In typical embodiment the limbs/legs of the joining profile enclose between 60° and 220°. Through this the limbs/legs do not run parallel to each other. That means, the limbs/legs project from each other or taper on top of each other. This results in the advantage that the individual limbs/legs can take up the tasks like compression, fixing, positioning and/or guidance.

Even an increase in compression is possible through graduated limbs/legs and these are provided in preferred embodiment.

In typical embodiments, the limb or the limbs/legs present or presents depressions, grooves, perforation, slits and/or longitudinal holes. This results in advantage that the limbs/legs can take over the tasks like fixing or positioning. Another advantage is that through the special limb form the joining profile preferably acts like spring and creates a compression. Advantageously, the coalescing of the joining profile with bones is improved through the above-mentioned limb form.

In typical embodiments the free ends of the limbs/legs are designed with a tip and/or with a bevel. Preferably, the limbs/legs present spike and/or barb. The advantage through this is that the placement of the joining profile is simplified and the joining profile is positioned better and secure in the bones.

Advantageously, the surgical instrument comprises a striking surface. The striking surface preferably emerges after breaking the grip part at the joining profile. This results in the advantage that the joining profile can be inserted into the bones and/or tissues after breaking off the grip part with another tool, with which impact is made on the impact surface.

In typical embodiment the joining profile comprises an assembly. Preferably, the assembly is designed with an impact surface. This gives the advantage that the joining profile with the grip part, or even when the grip part is already broken, can be inserted further into the tissue and/or bone through another tool with which the impact surface is hit.

Advantageously, the grip part comprises an impact surface. This gives the advantage that the surgical instrument can be inserted in to the bones and/tissues through the impact surface on the grip part, preferably through another tool.

Advantageously, the impact surface of the grip part is an assembly structure. This results in the advantage that the grip part and the impact surface can be created as a single part.

In typical embodiment, the surgical instrument presents a drill. Preferably, the grip part presents a bore/hole. Especially, the surgical instrument preferably presents a multitude of bores/holes.

The bores preferably serve as drilling template for the shafts of the insertion element. It is also possible to insert other selected drills for fixing the bones and drilling templates.

This has the advantage that through the drills in the grip, the grip can be positioned at drill wire that is already inserted in the body. Thus, the surgical instrument and/or the joining profile can be positioned against the drill wires or the already existing bores.

In typical embodiments, the staple as well as the implant is designed in tubular form or partly in tubular form, e.g., as round or polygonal profile. These are preferably made of a pipe are solid matter preferably in round form. Preferred manufacturing processes are laser or spray process, in doing so, all variants are possible here.

In typical embodiments, the implant comprises, for instance, the staple, spikes. The spikes are preferably arranged between the limb and the staple. Through the spikes it has the advantage that with these additionally soft tissues, sinews or ligaments can be fixed at the bones.

In typical embodiments very small staple-designs with tubular or partly tube-like materials as described above are manufactured. These are inserted preferably with the aid of a guidance pipe or a cannula with a diameter smaller than 4 mm in to the body. These have the advantage that the staples can be inserted with the aid of a "mini open" process or percutaneous through a specific access. This has the advantage that the process can be used for joining the cracks in a meniscus. This is quicker and simpler than a process with braces and a suture.

In typical embodiment, the implant comprises, especially the staple, a lateral bracket/plate with a bore. Thereby this gives the advantage that an additional securing of the staple is possible with a screw.

In typical embodiment, the implant comprises, especially, the staple has at least one pin and/or a bracket with a bore between the limbs/legs as fixed space holder, thus the pin specifies a fixed angle correction or a fixed space.

In typical embodiments, the staple comprises a notch and/or a bore. Preferably, in this an instrument can be used. This has the advantage that the staple can be easily removed after the healing or with a revision. Preferably, the notches or the bores help as pre-set breaking point so that the user can separate this, for example, with a side cutter. The advantage is that for removal of this separated piece only small accesses have to be made, which is aesthetic and heals quickly.

In typical embodiments a drilling template comprises at least one slit, e.g. a V-slit or a Z-slit with different angles. Preferably, the drilling template is designed as saw template with a sideward contact for the saw blade. Alternatively, the surgical instrument presents a breakable separate saw template at the grip with at least one fixing bore and/or navigation help.

In typical embodiments, the staple and/or the implant comprise a multitude of limbs/legs. Preferably, the staple comprises a plate, especially a compression plate between the limbs. Preferably, the plate presents a multitude of bores. Especially, the bores help in fixing with bore wires and/or for screwing the bone parts. The advantage with this design in comparison with the fixing of bone parts with plates and nails and/or screws is that with the usage of a staple with limbs/legs lesser screws are used and through the design of the limb/leg a continuous compression is achieved, which is never possible with plates. Furthermore, it is advantageous that a staple is quick to be assembled and dismantled.

In typical embodiments, the plate design is preferably adjusted to suit the bone surface. As a result this has the advantage that the different requirements at the bone structure can be fulfilled. For instance, the plate is designed as a straight or almost straight plate as per case of application.

In typical embodiments, the implant is designed as almost straight plate and additionally as elbowed and/or bent in order to be able to compensate the angles and radii or as plate with levels, especially for comparison of height differences.

In typical embodiments, a pin is formed on the plate. Preferably, the pin is arranged between the limbs/legs. This has the advantage that the pin allows a specific angle correction or a specific distance.

In typical embodiments, the surgical instrument comprises a breakable pipe and/or saw template. Preferably, this comprises a fixing bore and/or a navigation help.

In typical embodiments, the implant is a anchor. Anchors are preferably made of round solid material, small tubes and in flat forms from all medically permissible materials. Mostly, they present some threading-like or some kind of indenting at the surface in order to anchor the implant securely in bones. Even dowel like designs are possible, which expand after insertion. This has the advantage that the anchor can be inserted in a simple manner. Till now, while inserting the anchors the problem of secure fitting of bands was always there, together with the complexity and handling of the associated setting instruments.

In addition, it is advantageous that the surgical instruments can be manufactured as single part and therefore in cost-effective manner. This is an immense advantage with a single-use product when all OP-relevant parts can be prepared as sterile packed, and no expensive, but if at all, only very few instrument sets are required.

In typical embodiments, the anchor is created from round, partly solid material or a small tube. Preferably the anchor is created as dowel shaped and/or in flat forms. For manufacture, all medically permitted materials are suitable.

In typical embodiments, the superficial surfaces present a threading and/or an indenting. This has the advantage that the anchor can be securely fixed in the bones.

In typical embodiments, the surgical instrument comprises a double anchor as implant. This has the advantage that, for instance, a strap can be pre-stressed in a device with specific tension and then used in a defined space in two bone parts. Preferably, as with all other variants fixing bores, diagonal fixing bores, a drill, a saw template as well as a navigation device are integrated to the anchor or to the shaft.

In the embodiments, the anchor presents an anchor leg made of plastic or absorbable material. Preferably, a joining web at the anchor is extruded. This has the advantage that additional suture material can be dispensed with.

Each anchor limb presents a separable extension shaft. This has the advantage that a multitude of anchors can be folded, bent, arranged next to each other and/or behind each other as in a magazine. This is advantageous, because the anchor made of a cannula can be employed as magazine especially for "suturing" cracks. The advantage is that no expensive knotting technique have to be used. The whole operation is possible with an instrument and an implant.

In typical embodiments the implant is a clamp. Clamps are used in various sizes with open and minimal invasive operations for joining blood-carrying vessels, intestines and organs. The hollow shaft-holding instruments for this purpose mostly present a diameter of 5 mm to 12 mm.

Mostly, many clamps are set on both sides at the point, where an organ is to be cut.

Preferably, clamps are created in partly round, partly polygonal, and in other forms from all materials that are permissible for medical purposes. Preferably, the clamps comprise a lock, in which both the clamp arms lock, when these are pressed together. The snapping takes place preferably with reaching a specific locking force. The clamps are preferably made of plastic.

In typical embodiments the clamps are made of titanium. Preferably, the material characteristics are selected in such a way that the clamps retain the shape after pressing.

The problem is that the clamps are very small parts. The removal from the magazine and holding in the jaw parts of the instrument up to OP-point is difficult because with the designs made of titanium there is no locking to be integrated against falling down.

In typical embodiments, the grip comprises a coupling, suitable for joining with grip. Consequently, this has the advantage that each user can join his preferred grip.

In typical embodiment, a grip is made as a single part at the grip part. This has the advantage that the surgical instrument can be manufactured in simple manner and can be offered as a unit in sterile packing.

In typical embodiment the clamps comprise a first shaft and as second shaft. Preferably, the shaft presents a diameter smaller than 5 mm, preferably 3.5 mm. This has the advantage that many shaft instruments can be inserted through a small opening, especially through the navel.

In typical embodiment, the shaft is designed as blunt. This has the advantage that no tissue is damaged.

In typical embodiment, the shaft is partly elbowed and/or bent in a radius. This has the advantage that the clamp is arranged in a separable extension, in the process the extension can be designed in flexible manner as per usage.

In typical embodiment the shaft is created from a flexible and pliable material. This has the advantage that the user can bend the clamp in preferred curvature before placing the clamp in the shaft in order that it makes it better at the OP-place without having to create new access points.

In typical embodiment, the shaft form is designed in such a way that a multitude of clamps, preferably up to six clamps are ready at the same time to be locked and/or set next to each other.

In typical embodiment the coupling is not arranged in shaft but outside the shaft. This has the advantage that a loading mechanism bigger than the implants can be developed for the clamps.

Preferably the multiple clamps are joined with each other. Preferably, the clamps are joined side wards with each other in the direction of insertion. Alternatively, the clamps can be arranged one behind the other and joined with each other. This has the advantage that the clamps can be taken out of the magazine in a simple way.

Preferably, the clamp is made of a composite material. Preferably, one of the materials is absorbable. In typical embodiment, the separable extension comprises a coupling for accommodation into a grip part.

In typical embodiment, the implant is a cage. Such a case is for instance disclosed in the patent document DE 10 2011 002 076. Preferably, cages are used for stabilising and spacing of the vertebrae. However, it is important that these cages are especially suitable for the following insertion process: "mini-open" and percutaneous. This includes the surgical instrument, preferably a guiding tube, for This has the advantage that the cage can be arranged in a specific angle, especially can be navigated well and can be expanded in parallel. This cage execution can be applied also in other medical fields, for instance, for hollow space creation for kyphoplasty, veterinary medicine and non-medical fields.

Preferably the cage comprises a top shell and a bottom shell. The top shell and the bottom shell are preferably joined through an adjusting device in displaceable manner. Preferably, the adjustment device is a pin This has the advantage that a space of the top shell to the bottom shell can be changed through simply pushing of the pin.

In typical embodiment, as adjustment device a pin, a spindle, an air pillow, a gel pad or a strip. This has the advantage that the cage can be used for dynamic joining of vertebrae.

A grip part is joined with the cage as implant through one pre-set breaking point at the minimum.

At least the bottom and/or top shell and/or, for instance, the pin are provided with a plate with at least one fixing bore in order to reinforce the vertebrae. Preferably, both plate sides join each other in positive fitting, in order to be able to accommodate greater force. Alternatively, even a locking plate can be additionally screwed in or integrated with a separable joining.

Preferably, at least the bottom and/or top shell and/or, for example, the pin is equipped with a staple leg or a staple plate with fitting bores in order to reinforce the vertebrae, in the process preferably both sides of the staple leg join each other in positive fitting. Alternatively, locking plate can also be screwed-in or integrated with a separable joint.

In typical embodiment, at the joining point between the implant and the grip, preferably further tasks like insertion, navigation, creation and fixing of cages can be exercised before breaking-off the grip part.

In typical embodiment, the cage comprises contact areas. The contact areas are preferably suitable to accommodate the applied pressure with the separation or hammering of the cage.

In typical embodiment the instrument comprises a coupling at one end, suitable for joining with a positioning instrument. As a result, this has the advantage that the manufacture can be made in cost-effective manner.

Alternatively, the instrument can be joined with a grip. Preferably the grip and implant are created from a material. Preferably, laser cutting, eroding, chipping or spraying are used as manufacturing process.

After insertion of the cage, and in an inter-vertebral disc this can be rotated in a specific angle laterally in preferred direction through the connections for navigation and the pull exercised on this. For this purpose, at the grip a graduated disc, not illustrated here, can be arranged, which enables the user to control and/or maintain the desired angle.

In typical embodiment, the instrument comprises an arrester or a notch. This has the advantage that a user recognizes and/or perceives, whether the desired angle is achieved and the cage can be expanded.

In typical embodiment, the pre-set breaking point is designed in such a way that the breaking and/or separation of the joining after expansion of the cage takes place preferably with the reaching of a definite force or a definite torque. Preferably, the grip part is separated.

Preferably, the wedge is designed in such a way that, if the expansion of the cage is not achieved at a specific position, the highest point of the wedge is skipped. This has the advantage that the cage is recoiled and can be removed in a better manner.

The pre-set breaking point is designed in such a way that the process of separation can trigger a definite movement. Examples for these movements can be a rotational movement or a linear movement. Under the conditions, the tool, for instance in the form of a drill bit or a forceps can be used for separation of the pre-set breaking point.

Preferably, the instrument comprises a tape suitable for joining the pats to be detached. This has the advantage that the detached parts can be controlled in order to prevent this from damaging the surrounding tissues, injure and/or from losing them.

In typical embodiment, the instrument is created from multitude of materials. This has the advantage that all elements can be created from the material with features beneficial for their function.

In typical embodiment, the instrument comprises a tube/rod with a cage, suitable for exercising a navigating movement. Preferably, the tube/rod can be joined with the cage. Especially, the tube comprises a shape memory alloy as material, especially Nitinol or it is designed as a string, suitable to navigate the cage through pull movements. Preferably, the cage presents drilled bores or holding points. This has the advantage that the string or a rod can be fitted in a simple manner.

A separate claim is asserted for a placement instrument for placing the surgical instrument described here.

Preferably, the positioning instrument comprises a grip. This has the advantage that the positioning instrument is easy to operate and manipulate for a surgeon.

Advantageously, the positioning instrument comprises a guiding groove for the surgical instrument with implant. Preferably, the grip is inserted in to the guidance groove. Advantageously, the joining profile can also be guided in to the guidance groove. The guidance groove is especially suitable for insertion of the grip part and subsequently for inserting the joining profile. Further the positioning instrument comprises two or a multitude of guidance grooves. This has the advantage that the surgical instrument can be securely guided with the positioning instrument.

In typical embodiment, the positioning instrument has an impact surface. This has the advantage that with the positioning instrument the surgical instrument can be inserted in hard stuff, like bones.

Advantageously, the positioning instrument comprises support surface. Preferably, the support surface can be brought to the impact surface of the joining profile and/or the impact surface of the grip in active connection. This has the advantage that the hits, which are made on the impact surface of the positioning instrument, are transferred securely and in a guided manner and mainly in correct angle on the surgical instrument, especially the grip part and/or the joining profile. This has the advantage that the grip part is prevented from breaking-off from the joining profile while giving the hits on the impact surface of the positioning instrument.

Advantageously, the support surface comprises a guidance groove. This has the advantage that the surgical instrument lies securely on the support surface of the positioning instrument and can be guided.

Separate claim is asserted for a drilling template for positioning the surgical instrument described here.

Preferably, the drilling template comprises a template, preferably with grip, suitable for positioning of bores in which the joining profile of the surgical instrument is positioned. This has the advantage that the pre-drilling of the openings for the joining profile is simplified.

Another embodiment describes a drilling template for positioning a surgical instrument, in doing so, a template, suitable for positioning of drills, for fixing bones, is used.

In typical embodiments the drilling template comprises a template, suitable for positioning of bores, for fixing of bones. Preferably, in the bores guide wires are provided. This has the advantage that the surgical instrument can be positioned through the drilling template and with the aid of the guide wire provided in the bores, that were drilled comparatively easily in advance, for positioning of joining profile. Consequently, finding the bores for the joining profile is simplified.

In typical embodiment, the drilling template comprises one or more guidance area(s) and/or guidance groove (s) for guiding the surgical instrument. Preferably the guidance area is suitable for guiding the joining profile. Especially, the guidance area is preferably suitable for guiding the grip part while positioning the joining profile. This has the advantage that the joining profile is guided and can be arranged in a definite angle in the tissue.

In the following, the invention is described in brief with the help of attached figures, in the process the figures show:

Figure 1:
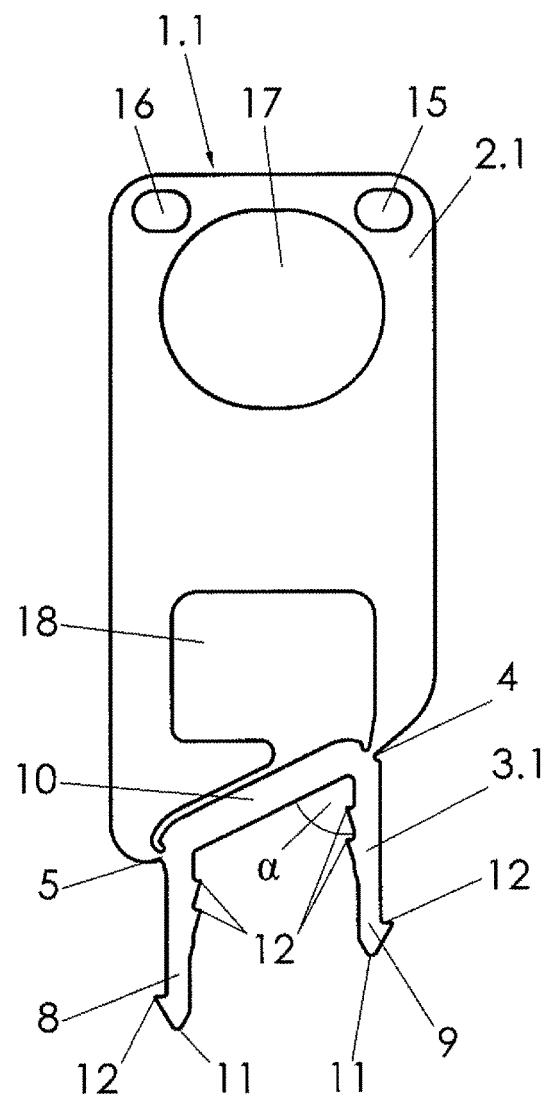
FIG. 1 shows a front view of a surgical instrument as per the invention with a grip and a joining profile.
Figure 2:
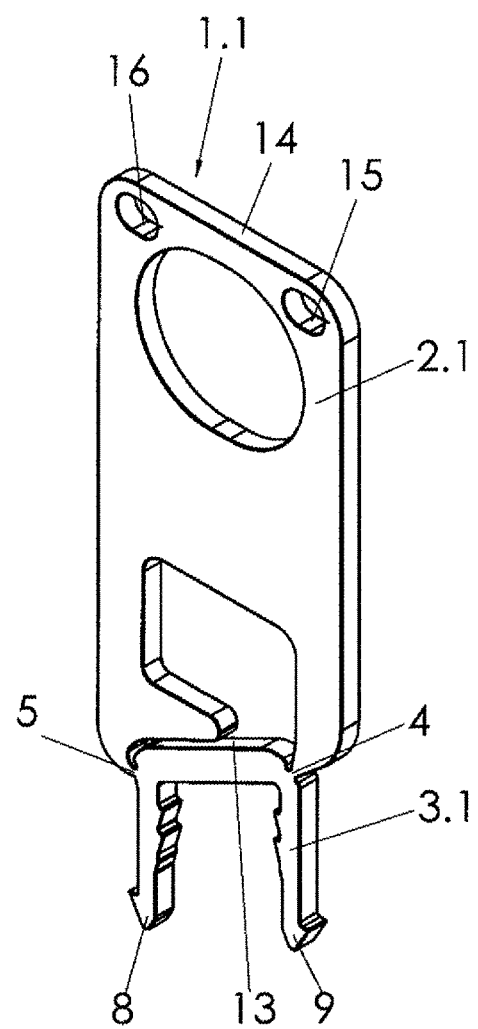
FIG. 2 shows a perspective illustration of the surgical instrument as per FIG. 1.

The FIGS. 1 and 2 disclose a surgical instrument 1.1. The surgical instrument 1.1 comprises a grip part 2.1 and a joining profile 3.1. The joining profile 3.1 comprises a first leg 8 and a second leg 9. The grip part 2.1 is joined with the joining profile 3.1 through a first pre-set breaking point 4 and a second pre-set breaking point 5.

The first leg 8 and the second leg 9 of the joining profile 3.1 are connected through a web 10. The leg 9 and web 10 of the joining profile 3.1 close-in at an angle α. In the present embodiment of FIGS. 1 and 2 the angle extends to α 26°. The free ends of the leg 8 and 9 each present a tip 11. The tips 11 are preferably smoothened. Furthermore, each leg 8 and 9 comprises a multitude of barbs 12.

The joining profile 3.1 comprises a joining profile impact surface 13. The joining profile impact surface 13 is found on the top surface of the web 10 of joining profile 3.1

The grip 2.1 comprises a grip impact area 14. The grip impact area 14 is found on the top side of the grip 2.1 Furthermore, the grip 2.1 comprises two template bores 15 and 16. Additionally, the grip 2.1 comprises a circular recess 17 and a rectangle recess 18, in the process, the rectangle recess 18 is designed in such a way that it forms the pre-set breaking points 5 and 4 between the grip 2.1 and joining profile 3.1.

Figure 3:
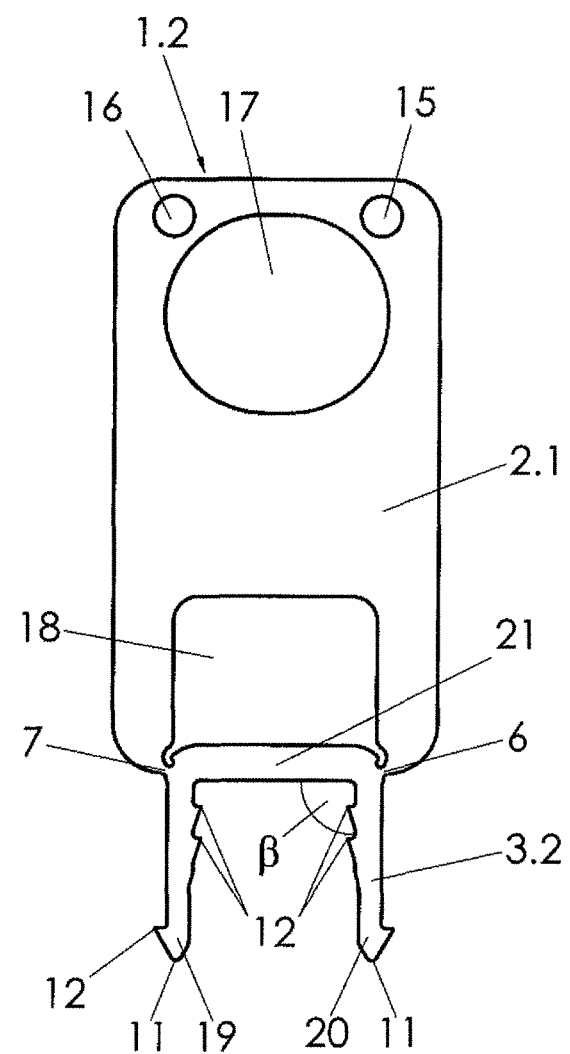
FIG. 3 shows a front view of another embodiment of invention-based surgical instrument with a grip part and a joining profile.
Figure 4:
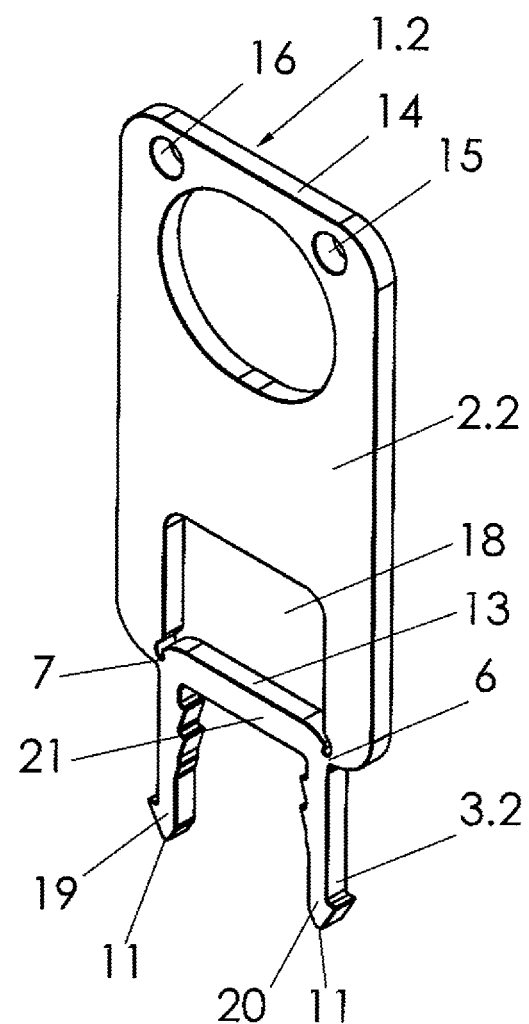
FIG. 4 shows a perspective illustration of the surgical instrument as per FIG. 3.

The surgical instrument 1.2 of FIGS. 3 and 4 is similar to the surgical instrument 1.1 of the FIGS. 1 and 2. The essential difference is that a joining profile 3.2 is formed in right angle, i.e., a first leg 19 and a second leg 20 of the joining profile 3.2 join with the web 21 of the joining profile 3.2 in an angle ??β, which is 90. All other parts of the surgical instrument 1.2 are similar to parts of the surgical instrument 1.1 of the FIGS. 1 and 2 and retain the same reference numerals. It is understandable that a grip 2.2, of the surgical instrument 1.2 differs from the grip 2.1 so that at the 90° joining profile can be joined.

Figure 5:
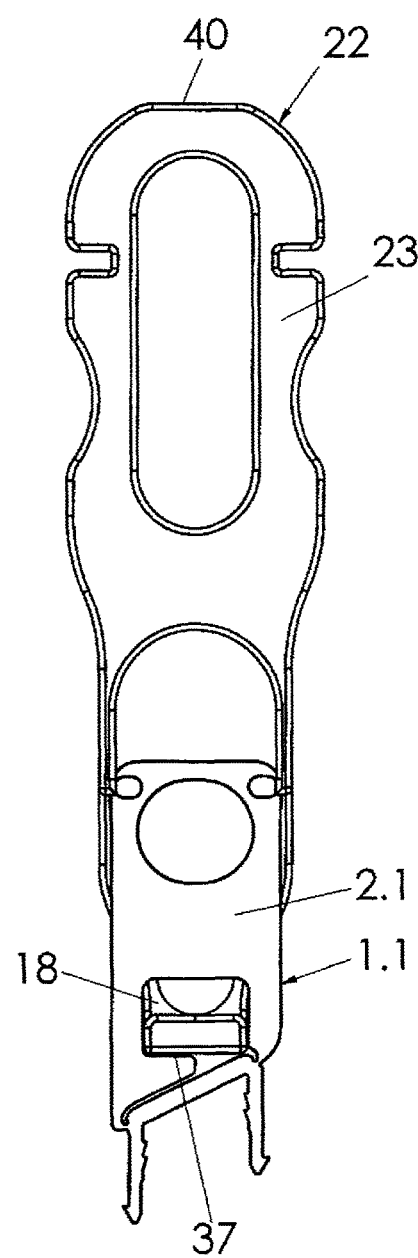
FIG. 5 shows a front view of a positioning instrument as per the invention with a surgical instrument as per the invention.
Figure 6:
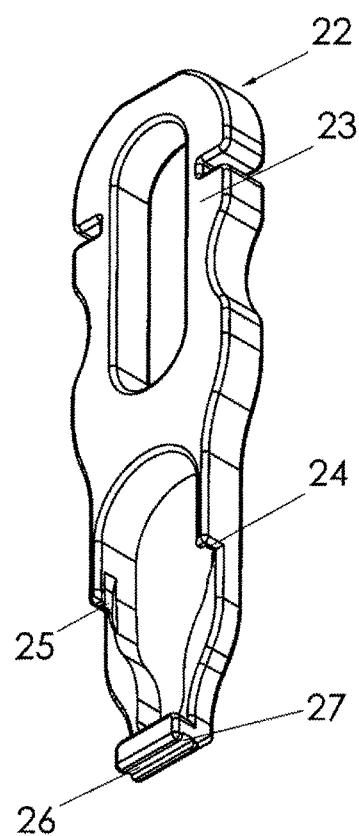
FIG. 6 shows a perspective illustration of the positioning instrument as per the invention without the surgical instrument.

FIG. 5 discloses a positioning instrument 22 as per invention with surgical instrument 1.1. The positioning instrument 22 as per the invention comprises, as shown in FIGS. 5 and 6, a grip 23. On the top side of the grip 23 the positioning instrument 22 comprises an impact surface 40. Additionally the positioning instrument 22 comprises a first guidance groove 24 and a second guidance groove 25 for grip 2.1 and 2.2.

As shown in FIG. 6, the grip 22 comprises a supporting area 26 at the end of the joining profile. The support area 26 is suitable for attachment at joining profile impact surface 13 or the grip impact surface 14 of the surgical instrument 2.1 and 2.2. Additionally the support surface 26 of the positioning instrument 22 comprises a guidance groove 27. The guidance groove 27 is suitable to grip top side of the grip 2.1 or 2.2 and to guide.

Figure 7:
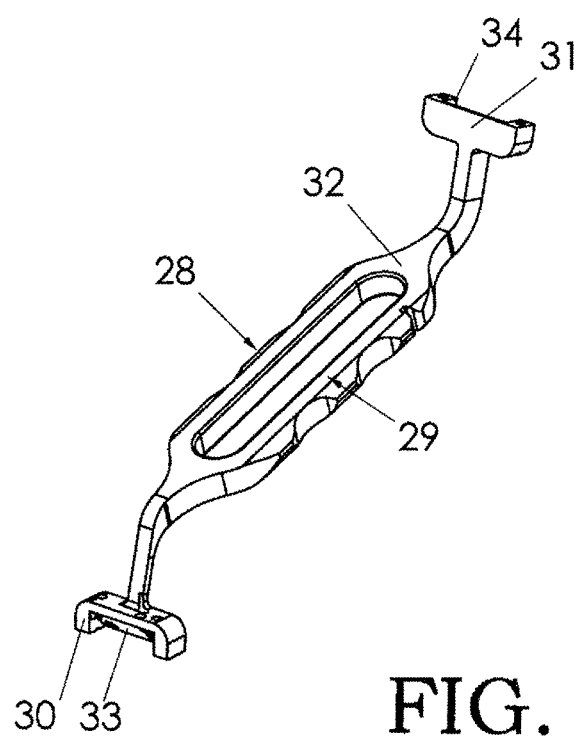
FIG. 7 shows a perspective illustration of a drilling template as per the invention.
Figure 8:
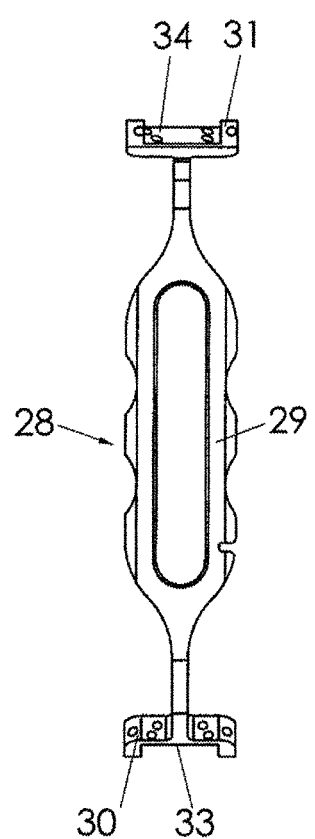
FIG. 8 shows a front view of the drilling template as per the invention as per FIG. 7.

FIGS. 7 and 8 show a drilling template 28 as per the invention. The drilling template 28 comprises a grip 29 for good handling of the drilling template 28. At its first end the drilling template 28 comprises function element 30. At its second end the drilling template 28 comprises a function element 31. The function elements 30 and 31 present respectively a multitude of template elements and guidance elements. Both the function units 30, like the function element 31 present respectively one guidance surface 33 and 34 for the surgical instrument 1.1 or 1.2.

The functions unit 30 protrudes from grip 29 of the drilling template 28 in a manner that the function unit 30 can be inserted in to the body of the patient when a surface 32 of the drilling template 38 points the treated patient. When the top surface 32 of the drilling template 28 points towards the patient, the functions unit 31 can be applied as template.

Figure 9:
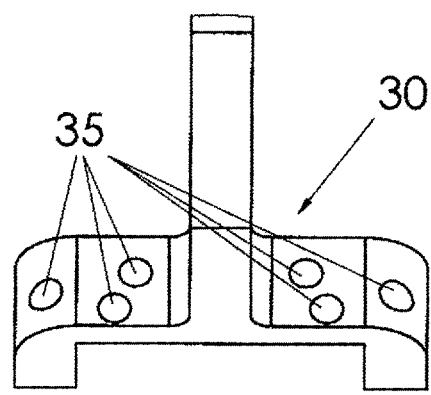
FIGS. 9-12 show an enlarged section of the invention-based drilling template as per FIG. 8.
Figure 11:
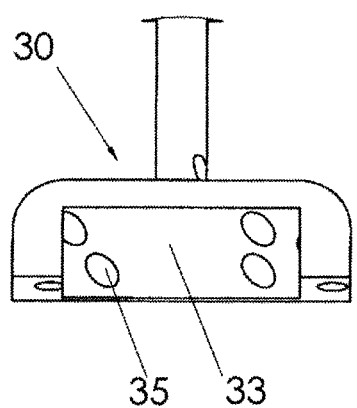
Figure 12:
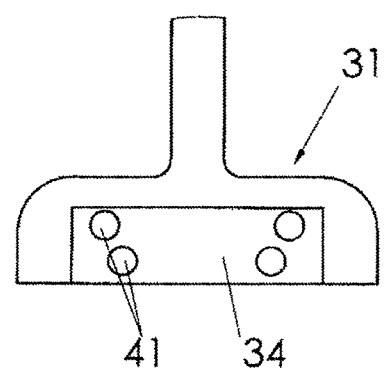

FIG. 9 shows an enlarged top view of the functions unit 30 of the drilling template 28. This comprises a multitude of bores 35, which are suitable as templates for insertion of the so-called 90° joining profiles, also to the surgical instrument 1.2. Suitable to this, FIG. 11 discloses a bottom view of the functions unit 30, with bores 36, which is suitable for insertion of surgical instrument 1.2. Both the bores 35 and the bores 36 are inserted in a right angle to a surface of the functions unit 30. In FIG. 11, the bores 36 appear conical, because they lie in the slant guidance area 33 of the functions unit 30.

Figure 10:
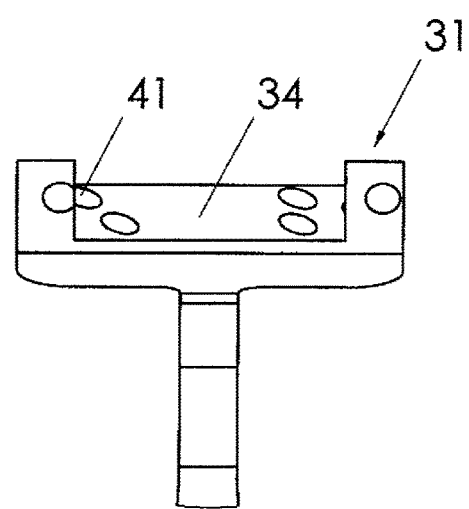

FIG. 10 shows a top view of the functions unit 31, which is suited as template for surgical instrument 1.1. That is why, the bores 41 and in angle α, designed preferably in 26°. With the help of the functions unit 31 of the bore template 28, the bores in suitable angle are created for the leg 8 and 9 of the joining profile 3.1 of the surgical instrument 1.1.

The functioning of the present invention is given below:

The surgical instruments 1.1 and 1.2 are implanted in the same type and manner. In the following, for reasons of clarity only the implantation of the surgical instrument 1.2 is described.

For implanting the joining profile 3.2 this is inserted with the surgical instrument 1.2 in the positioning instrument. For this the grip 2.2 of the surgical instrument 1.2 is guided into the guidance grooves 24 and 25 of the positioning instrument. Thereby the attachment surface 26 connects in to the rectangle recess 18 of the grip part 2.2, in such a way that the attachment surface 26 lies in the rectangle recess 18 and at the impact surface 13 of the joining profile 3.2. For better guidance the grip part 2.2 lies with its grip impact surface 14 in the guidance saw groove 27 of the positioning instrument 22.

Figure 13:
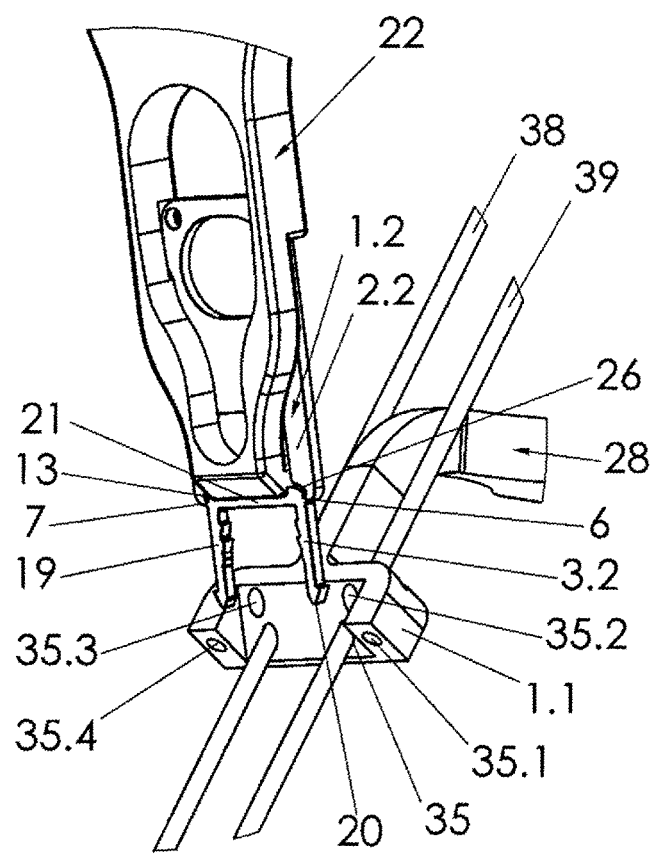
FIG. 13 shows a perspective illustration of the invention-based surgical instrument with an invention-based positioning instrument and an invention-based drilling template while inserting the surgical instrument in the tissue.

FIG. 13 shows the surgical instrument 1.2, that is accommodated in the positioning instrument 22, the drilling template 28 and a first guide wire 38 and a second bore wire 39. The guide wires 38 and 39 are already placed in the body tissue, preferably in bones.

In order to be able to position the surgical instrument 1.2 better, the drilling template 28 is guided with its openings 35 and through the first guide wire 38 and the second guide wire 39.

The free bores 35.1 to 35.4 as well as bores, in which the guide wires 38 and 39 are introduced, have many purposes. Further guide wires can be inserted for fixing the bone parts. Furthermore, the bores 35.1 to 35.4 serve partly as templates for drilling of openings for the leg 19 and 20 of the joining profile 3.2. For insertion of the joining profile 3.2 the guide wires 38 and 39 are partly taken out of the tissue and/or bones.

In order to insert the joining profile 3.2 in the bones, hits are applied on the impact surface 40 of the positioning instrument 22. When the joining profile 3.2 is inserted up to a specific depth, then the joining profile 3.2 can be separated at the pre-set breaking point 6 and 7 from the grip 2.2 through a rotation and/or bend movement.

Further there is the possibility to insert the joining profile 3.2 through hits on the impact surface of the joining profile 13 further into the tissue and/or bones.

Alternatively, the surgical instrument can be inserted directly into the tissue and/or bones in other embodiments not illustrated here without using the positioning instrument. Through the grip the joining part can be handled relatively well, so that there is the possibility that a surgeon grips the surgical instrument at the grip and the joining profile is partly inserted into the tissue through hits on the impact surface of the grip. Then, the surgeon can separate the grip at the pre-set breaking point from the joining profile. If necessary the joining profile can be inserted further into the bones through hits on the impact surface of the grip.

Figure 14:
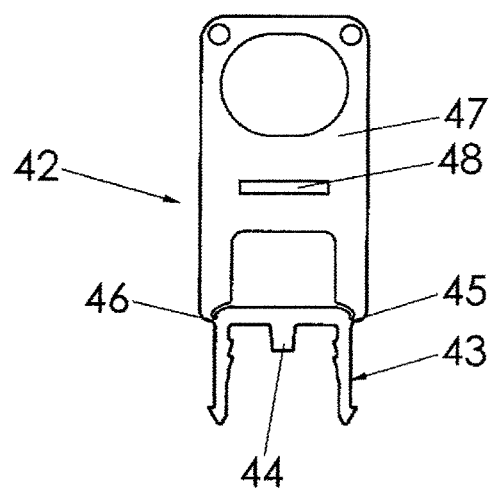
FIG. 14 shows a schematic illustration of a front view of a surgical instrument as per the invention with a staple as implant.

FIG. 14 shows a front area of a surgical instrument 42 with a staple 43 as implant. The staple 43 presents a wedge 44. The wedge 44 is suitable for angle correction. The staple 43 is connected through two pre-set breaking points 45 and 46 with a grip 47. The grip presents a slit 48. The slit 48 is suitable as saw template.

Figure 15:
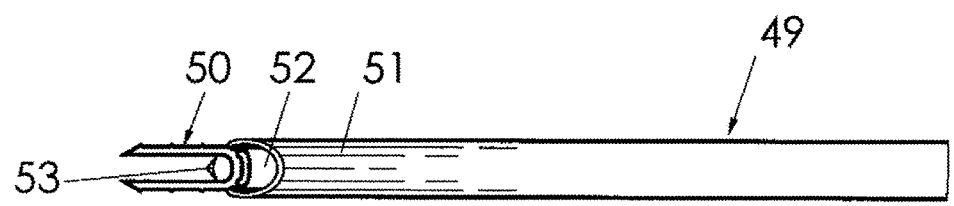
FIG. 15 shows a schematic illustration of another embodiment of an invention-based surgical instrument with a staple as implant and a cannula.
Figure 16:
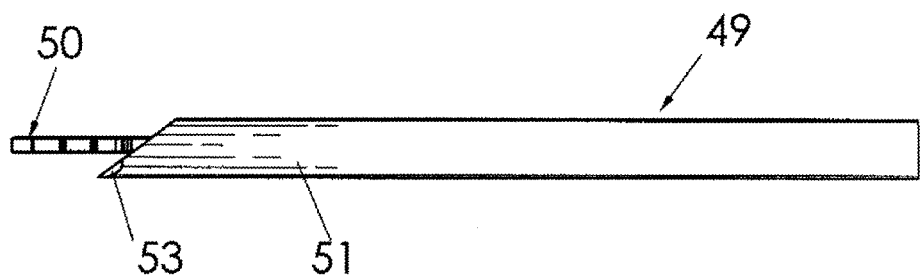
FIG. 16 shows a schematic illustration of a top view of the surgical instrument as per FIG. 15.
Figure 17:
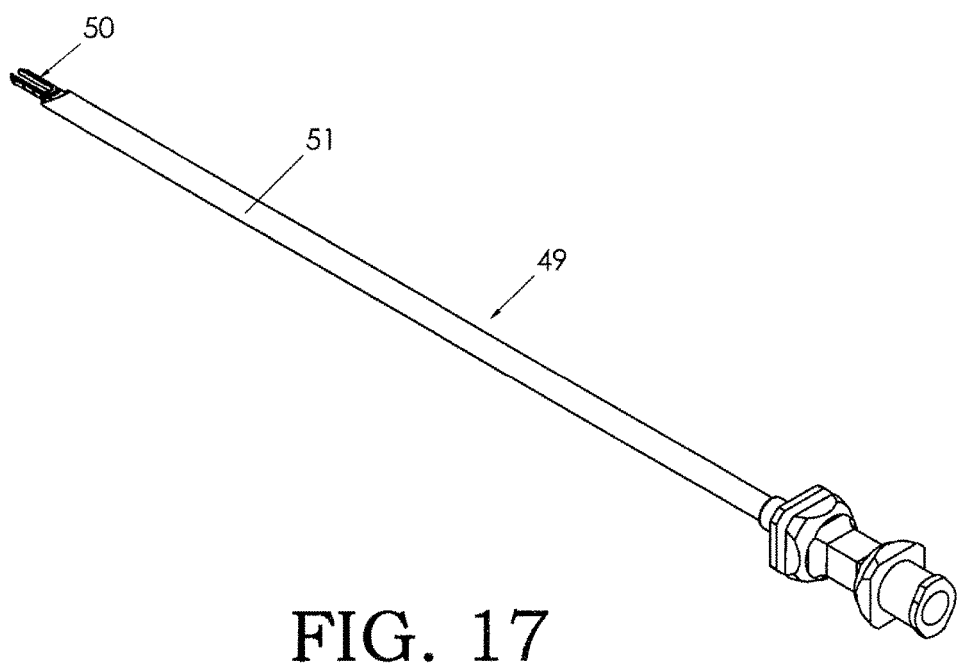
FIG. 17 shows a surgical illustration of a perspective view of the embodiment of surgical instrument as per FIGS. 15 and 16.

FIGS. 15, 16 and 17 show another embodiment as invention-based instrument 49. As implant a staple 50 is provided. The staple 50 presents a smaller size, preferably smaller than 4 mm. Additionally, the surgical instrument 49 presents a cannula 51. The surgical instrument comprises grip 52 and staple 50 and guided is guided into the cannula 51. The cannula 51 presents a sharp edge 53. This has the advantage that the surgical instrument 49 is also suitable for cutting. The embodiment of the surgical instrument 49, according to FIGS. 15, 16 and 17, is suitable for percutaneous fixing of smaller fragments of bones. Through the cannula 51, the staple 50 can be inserted without substantial damage to the surrounding tissue.

Figure 18:
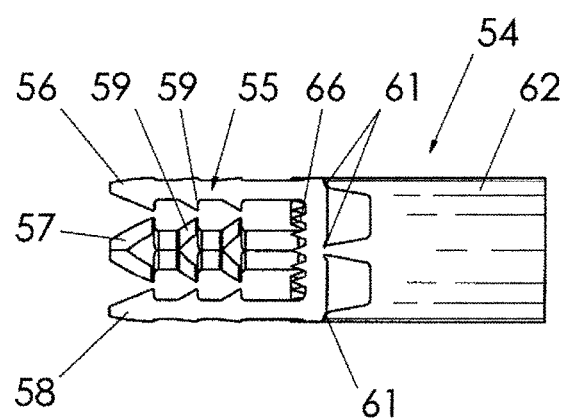
FIG. 18 shows a schematic illustration of a side view of another embodiment of an invention-based surgical instrument with a staple with spikes as implant.
Figure 19:
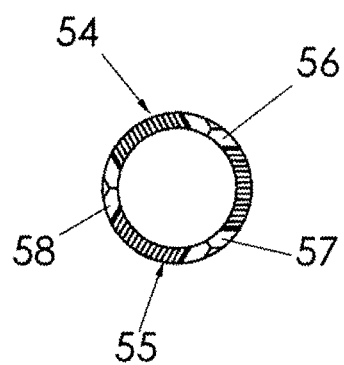
FIG. 19 shows a surgical illustration of a top view of the surgical instrument as per FIG. 18.
Figure 20:
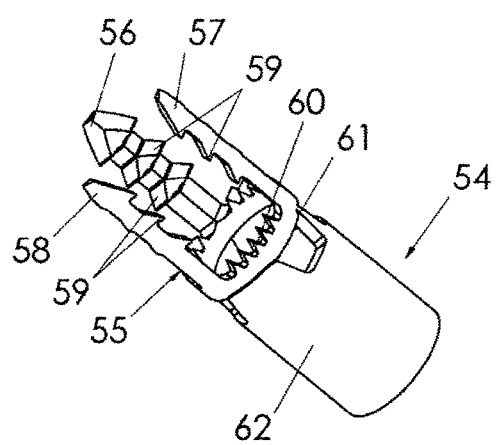
FIG. 20 shows a perspective illustration of the surgical instrument as per FIGS. 18 and 19.

FIGS. 18, 19 and 20 show another embodiment of a surgical instrument 54 as per the invention with a staple 55 as implant. The staple 55 is created from a pipe. The staple 55 presents three legs 56, 57 and 58, as can be recognized in FIG. 19. The staples 55 and/or the leg 56, 57 and 58 present barbs 59. Additionally, the staple 55 presents spikes 60 in its top area.

The staple 55 is connected through a multitude of pre-set break points 61 with a grip part 62. The grip 62 is tubular designed. Consequently, this has the advantage that the surgical instrument 54 can be created from a tube. For cutting off the unnecessary parts, preferably a laser process is applied.

Figure 21:
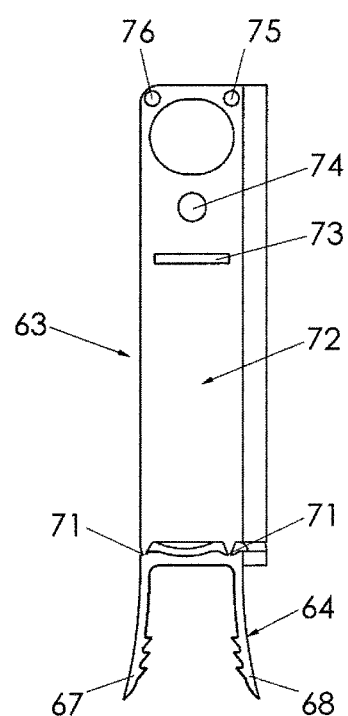
FIG. 21 shows a schematic illustration of a side view of another embodiment of a surgical instrument as per the invention, in the process, the implant is a staple with four legs.
Figure 22:
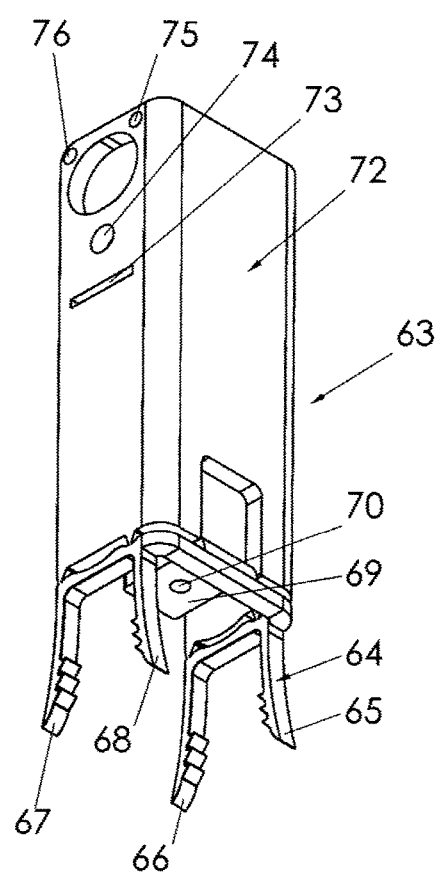
FIG. 22 shows a schematic illustration of a perspective view of surgical instrument with a staple with four legs as per FIG. 21.

The FIGS. 21 and 22 show another embodiment of a surgical instrument 63. The surgical instrument 63 comprises a staple 64 with four legs 65, 66, 67 and 68. Additionally the staple 64 comprises a plate 69 with a fixing drill 70. Through a multitude of pre-set breaking points 71 the staple 64 is connected with a grip 72. The grip 72 presents a slit 73, which can also serve as saw template. Bores 74 to 76 in the grip 72 serve as drilling template.

Figure 23:
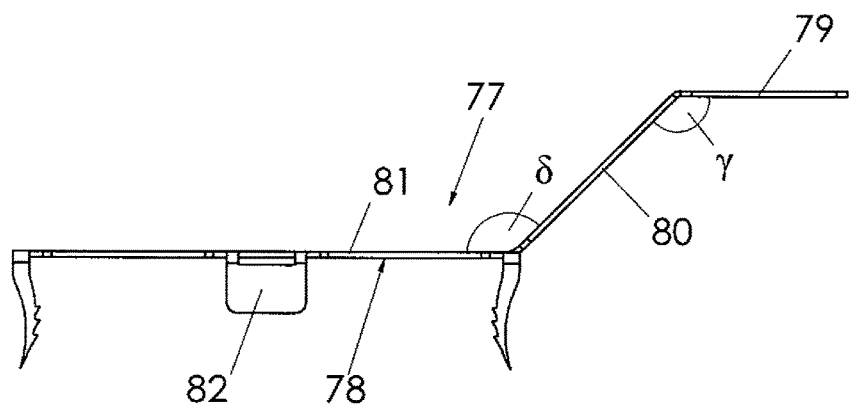
FIG. 23 shows a schematic illustration of a side view of another embodiment of the instrument as per invention with a staple with a staple plate and a lateral pin for angle correction.
Figure 24:
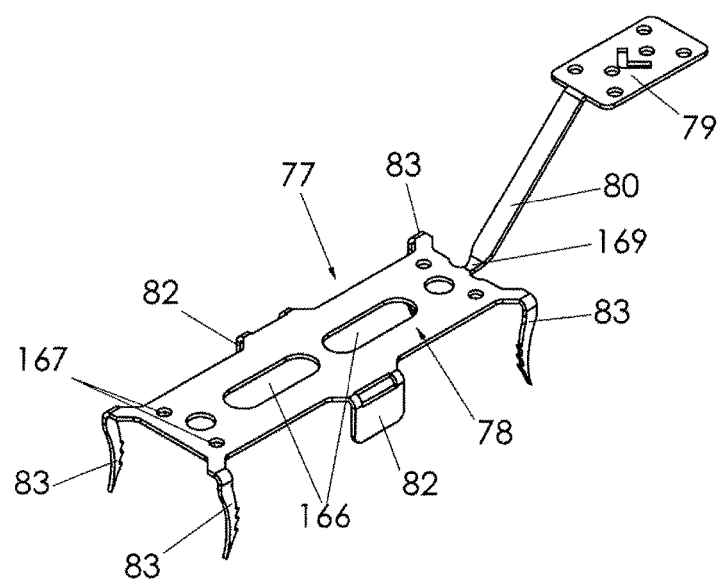
FIG. 24 shows a schematic illustration of a perspective view of the surgical instrument as per FIG. 23.

The FIGS. 23 and 24 show another embodiment of surgical instrument 77. The surgical instrument 77 comprises a staple 78 as implant and as grip a holding plate 79. The holding plate 79 is connected through a connecting pin 80 with the staple 78. The holding plate 79 is arranged in an angle γ to the connecting pin 80. The angle α lies preferably between 90° and 120°.

The connecting pin 80 joins with a compression plate 81 of the staple 78 in an angle δ.

The staple 78 comprises a compression plate 81. This presents a sideward wedge 82 for angle correction.

Additionally, the staple 78 comprises at each corner of the compression plate 81 a leg 83. Analogue to the embodiments described already, the holder plate 79 comprises openings 166 and slits 167, which serve the purpose as drilling template.

The functioning of the embodiments of the FIGS. 14 to 23 as per the invention is as follows:

The staple 43, 50, 55, 64 or 78 is positioned and then inserted into the tissue, preferably in the osseous material. When the staple 43, 50, 55, 64 or 78 is correctly positioned, grip 47, 52, 62, 72 or 79 is separated from the staple 43, 50, 55, 64 or 78 through the pre-set breaking point.

Figure 25:
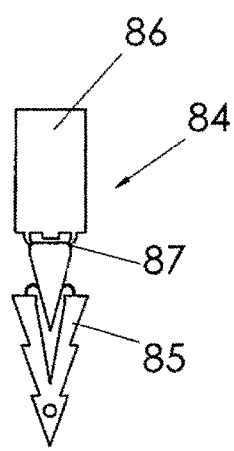
FIG. 25 shows a schematic illustration of a side view of another embodiment of a surgical instrument as per the invention, with which the implant is bolt.

FIG. 25 shows another embodiment as per the invention 84. The surgical instrument 84 comprises a bolt 85 as implant and a grip 86. The bolt 85 is connected through a pre-set breaking point 87 with the grip 86. In the illustrated embodiment the pre-set breaking point 87 is circularly designed. The functioning is analogue to the embodiments of surgical instruments described above.

In other embodiments not described here the surgical instrument 84 is inserted in a guiding tube, especially a cannula.

Figure 26:
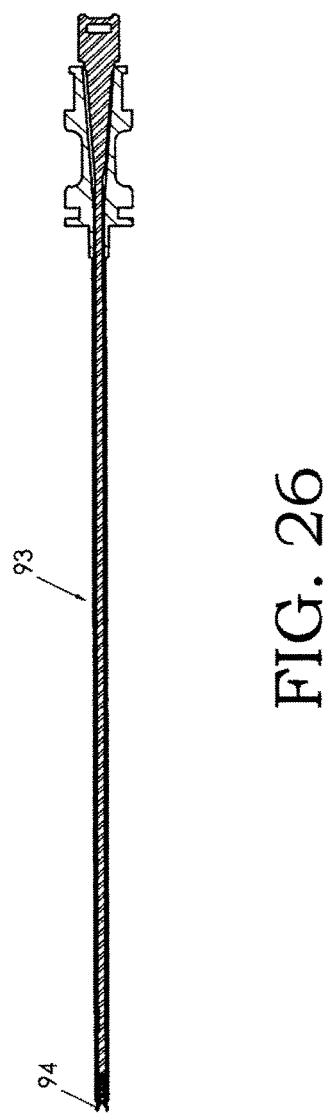
FIG. 26 shows a schematic illustration of a side view of another embodiment of the surgical instrument as per the invention, with which the implant is a clamp.

FIG. 26 shows another embodiment of a surgical instrument 93.

Figure 27:
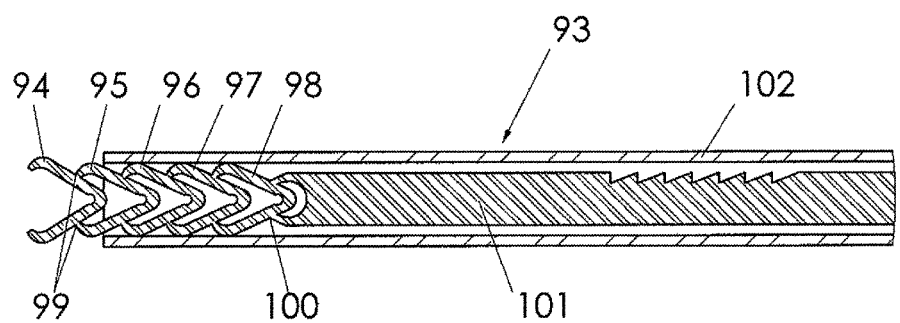
FIG. 27 shows an enlarged section of a front area of the surgical instrument as per FIG. 26.

The FIG. 27 shows an enlarged section of a front area of the surgical instrument 93. With this, as implant a multitude of clamps 94, 95, 96, 97 and 98 are provided. The clamp 94 is connected through a pre-set breaking point and/or through two pre-set breaking points 99 with the clamps 95. Similarly clamp 95 is connected with clamp 96. The clamp 98 is connected through a pre-set breaking point 100 with a grip 101. The grip 101 and the multitude of clamps 94 to 98 are guided into a cannula 102. The grip 101 can be connected through a coupling with an instrument handle not show here. Basically the grip 101 is formed as single part to the instrument grip.

With the embodiment shown in FIG. 27 the clamps 94, 95, 96, 97 and 98 can be brought out one after the other from a type of magazine.

Figure 28:
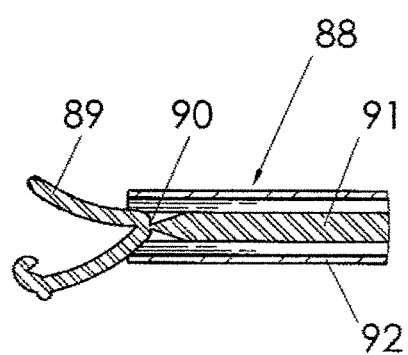
FIG. 28 shows a schematic illustration of a top view of front area of another embodiment of a surgical instrument.

FIG. 28 shows an enlarged top view of a front area of a surgical instrument 88. A clamp 89 is connected with grip 91 through a pre-set breaking point 90. The grip 91 and the pre-set breaking point 90 are guided into a cannula 92. The grip 91 can be connected through a coupling with an instrument grip not clearly shown. Basically, the grip 91 can be formed as a single part to the instrument grip.

Figure 29:
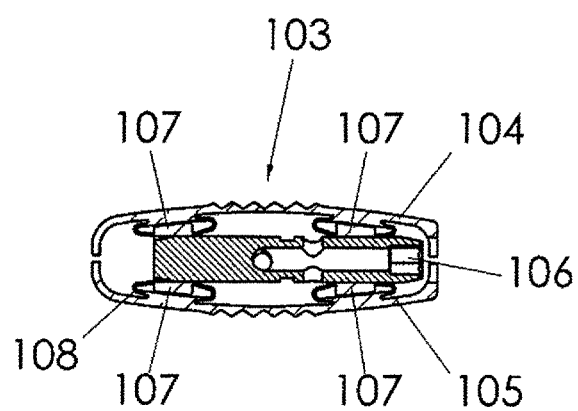
FIG. 29 shows a schematic illustration of a cut side view of a cage that can be expanded through a Spindle as per the state of the art.

FIG. 29 shows a cage 103 as implant as per state of the art. The cage 103 comprises a top shell 104 and a bottom shell 105. Through a connecting point 106 for a spindle not clearly shown, the cage 103 can be expanded. By actuating the connecting point 106 with a spindle, the wedge 107 is pushed. Thus the wedge 107 adjusts so that the cage 103 can be expanded. The top shell 104 is connected with bottom shell 105 apart from the wedges 107 through flexible tapes 108.

Figure 30:
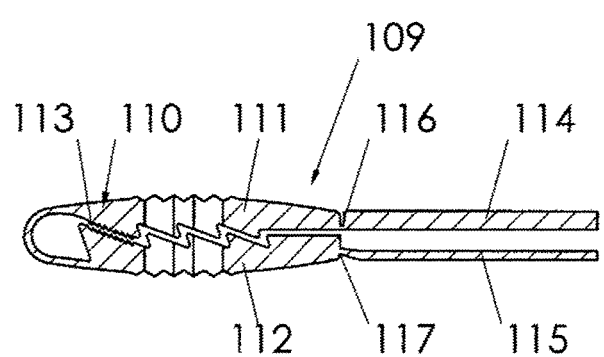
FIG. 30 shows a schematic illustration of a cut side view of an embodiment of a surgical instrument as per the invention with a cage as implant.
Figure 31:
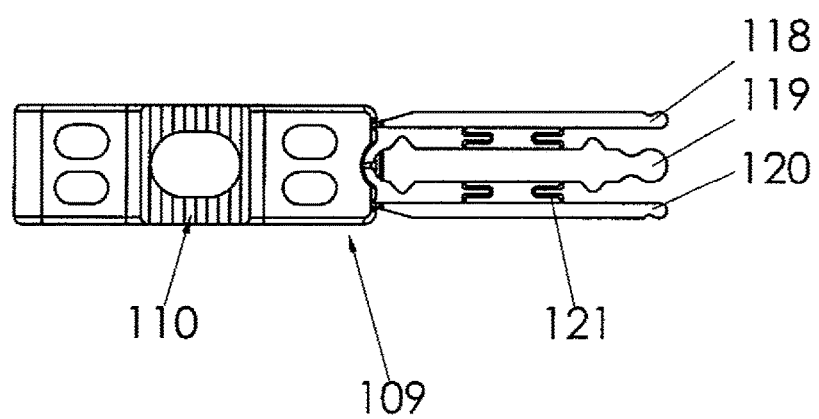
FIG. 31 shows a schematic illustration of a top view of the surgical instrument as per the invention with a cage as implant as per FIG. 30.

The FIGS. 30 and 31 show a surgical instrument 108 as per invention with cage 110 as implant. The cage 110 comprises a top shell 111 and a bottom shell 112. The top shell 111 and also the bottom shell 112 are connected with each other at the surfaces facing each other like multitude of smaller wedges, which form a zig-zag form and through a flexible tape 113. The flexible tape 113 is arranged between a tapered, inner sides of the top shell 111 and the bottom shell 112 facing each other. Preferably, the tape 113 is created from an elastic material.

For connecting the elastic tape 113 with the cage, the tape is preferably formed/moulded as single part with the cage. Alternatively, the band can be riveted or affixed to the cage. Additionally, the top shell 111 and the bottom shell 112 are connected as single part with each other through an elbow 117.

Thus, the top shell 111 is connected with the bottom shell 112 through at least one flexible tape 113, this has the advantage that no other expensive holding mechanism like joints or hinges have to be employed.

In other embodiments not illustrated here, the bottom and/or top shell possess at least one separable connection or present other separable connections.

As grip the surgical instrument 109 comprises two rods 114 and 115. The rod 115 is connected through a pre-set breaking point 117 with the bottoms hell 112 of the cage 110. The top rod 114 is again subdivided in to three strips 118, 119 and 120. The strips can fulfil various tasks and functions as per the width and stability, like navigation, control, expansion and/or coupling. The individual strips 118 to 120 are connected with each other through flexible tapes 121. Thus, while breaking the strips and/or rods 114, 115, 118, 119 and 120, this is prevented from injuring the tissues.

The functioning of the surgical instrument is as follows:

Through the rods 114 and 115 the cage 110 is correctly positioned and held. Then through a pull and/or pressure on the rods 115 the cage is expanded and/or the top surface 112 is spaced from the top shell 112. Through the strips 118 to 120 another alignment of the cage 110 and the shell 111 is possible through bottom shell 112. When the cage 110 sits correctly, the rods 114 and 115 are separated at the pre-set breaking points 116 and 117 from the cage 110.

Figure 32:
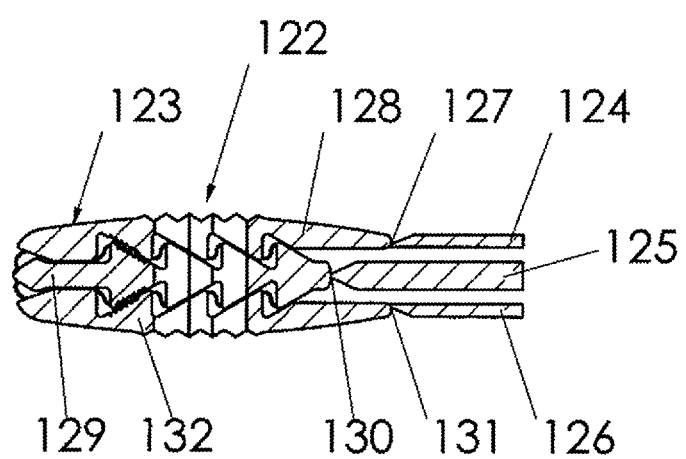
FIG. 32 shows a schematic illustration of a cut side view of another embodiment of the surgical instrument with a cage as implant as per the invention.

FIG. 32 shows another embodiment of a surgical instrument 122 as per the invention. The surgical instrument 122 comprises as implant a cage 123 and as grip three rods 124, 125 and 126. The cage 123 comprises as connecting element a wedge-chain 129. Additionally, the wedge-chain 129 is connected through a flexible tape 171 with the bottom shell 132 and through a flexible tape 172 with the top shell 128. The rod 124 is connected through pre-set breaking point 127 with a top shell 128 of the cage 123. The rod 125 is connected with the wedge-chain 129 through pre-set breaking point 130. The rod 126 is connected through a pre-set breaking point with the bottom shell 132 of the cage 123.

The functioning of the surgical instrument 122 is as follows:

Through the rods 124 and 125 the cage 123 is correctly positioned and held. Then through a pull and/or pressure on the rods 125 the cage 123 is expanded and/or the top surface 128 is spaced from the bottom shell 132. When the cage 123 sits correctly, the rods 124 to 126 are separated at the pre-set breaking points 127, 130 and 131 from the cage 123.

Figure 33:
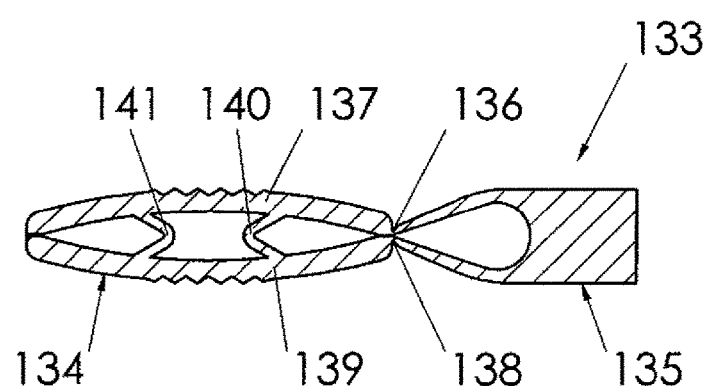
FIG. 33 shows a schematic illustration of a cut view of another embodiment of invention-based surgical instrument with a cage as implant in a non-expandable condition.
Figure 34:
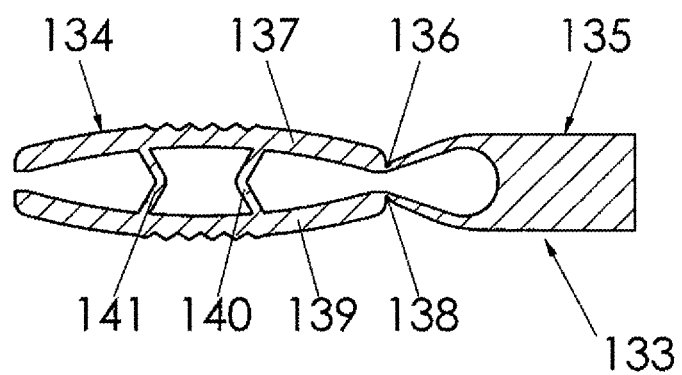
FIG. 34 shows a schematic illustration of a cut side view of the invention-based embodiment of the surgical instrument with a cage as implant as per FIG. 34, in the process the cage is in an expanded condition.

FIGS. 33 and 34 show another embodiment of a surgical instrument 133. The surgical instrument 133 comprises as implant a cage 134 and as grip a pulling or pressure rod 135. The pull/push rod 135 is connected through a pre-set breaking point 136 with a top shell 137 of the cage 134. The pull/push rod 135 is connected through a pre-set breaking point 137 of the cage 134. The pull/push rod 135 is connected through a pre-set breaking point 138 with a bottom shell 139 of the cage 134. The top shell 134 and the bottom shell 139 of the cage 134 are connected with each other through a first web 140 and a second web 141 directly. This has the advantage that the cage 134 could be created as a single part. The webs 140 and 141 serve the purpose of expanding the cage 134 through pull/push, in doing so, the web alignment can also run in one direction. For aligning the cage, the pull/push rod 135 serves the purpose.

In other embodiments not shown here, for aligning of cage an additional separate instrument can also be used.

Figure 35:
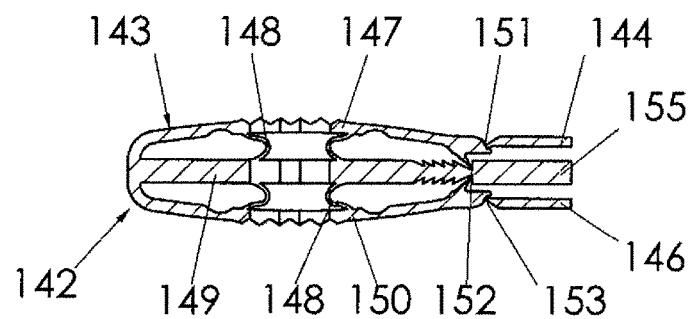
FIG. 35 shows a schematic illustration of a cut side view of another embodiment of surgical instrument with a cage as per invention as implant.

FIG. 35 shows another embodiment of a surgical instrument 142. The surgical instrument 142 comprises as implant a cage 143 and as grip three rods 144, 145 and 146. A top shell 147 of the cage 143 is connected through flexible tapes 148 with the central web 149. A bottom shell 150 is similarly connected through flexible tapes 148 with the central web 149. Through rods 144 to 146 the cage 143 is positioned. Through pull/push with the rod 143 at the central web 149 the top shell 147 and the bottom shell 150 are expanded from one another. When the cage 143 presents the correct opening width and is correctly positioned, the rods 144, 146 and 146 at the corresponding pre-set breaking points 151, 152 and 153 are separated from the cage 143.

Figure 36:
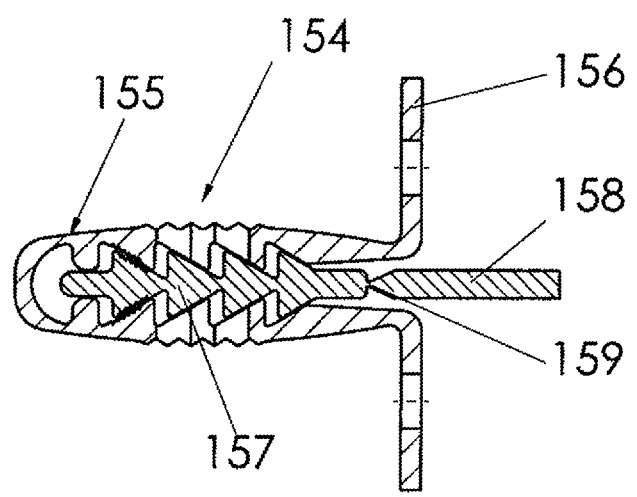
FIG. 36 shows a schematic illustration of a cut side view of another embodiment of the surgical instrument with a cage as per the invention as implant.

FIG. 36 shows another embodiment of a surgical instrument 154. The surgical instrument 154 comprises as implant a cage 155. The cage 155 comprises an integrated reinforcement plate 156. In the present embodiment, the cage 155 is adjusted through a wedge-chain 157.

As grip, the surgical instrument 154 comprises a rod 158, which is connected through a pre-set breaking point 159 with the wedge-chain 157.

In another embodiment not shown here, all forms of cages mentioned till now can be combined with a reinforcement plate.

Figure 37:
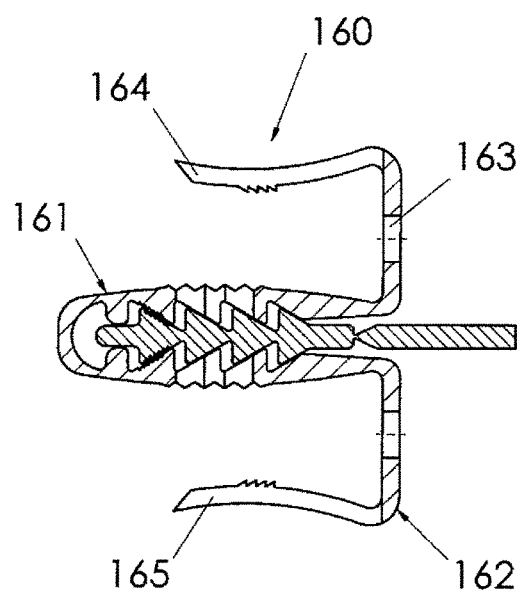
FIG. 37 shows a schematic illustration of a cut side view of another embodiment of surgical instrument with case as per the invention as implant.

FIG. 37 discloses another embodiment of a surgical instrument 160. The surgical instrument 160 comprises as implant a cage 161 with an integrated staple 162. The staple 162 comprises a staple plate 163 and two staple legs 164 and 165. A grip 168 is designed similar to the designs mentioned previously.

The invention claimed is:

1. A surgical instrument comprising:
    an implant comprising a joining profile configured to engage a portion of a bone, the joining profile including a first leg, a second leg, and a web, wherein the first leg is connected to the web forming a first elbow and the second leg is connected to the web forming a second elbow, and the second elbow forms an angle in a range of 15 degrees to 120 degrees between the second leg and the web; and
    a grip comprising a first recess and a second recess, wherein the second recess forms a first pre-set breaking point and a second pre-set breaking point, wherein the first pre-set breaking point and the second pre-set breaking point are configured in a depression of the joining profile;
    wherein the first pre-set breaking point connects a first portion of the grip to a first corner of the first elbow providing a connection point between the web and the first leg of the joining profile in the depression of the joining profile; and
    the second pre-set breaking point connects a second portion of the grip to a second corner of the second elbow providing a connection point between the web and the second leg of the joining profile in the depression of the joining profile.

2. The surgical instrument of claim 1, wherein the instrument includes a guidance tube.

3. The surgical instrument of claim 2, wherein the guidance tube comprises a cannula.

4. The surgical instrument of claim 1, wherein the implant comprises a staple.

5. The surgical instrument of claim 1, wherein a joining profile impact surface is provided on a top surface of the joining profile.

6. The surgical instrument of claim 1, wherein a grip impact surface is provided on a top side of the grip.

7. The surgical instrument of claim 6, wherein the grip impact surface is a component.

8. The surgical instrument of claim 1, wherein the grip includes bores.

9. The surgical instrument of claim 1, wherein the implant comprises a bolt or a clamp.

10. The surgical instrument of claim 1, wherein the grip comprises a rod.

11. The surgical instrument of claim 1, wherein a plurality of clamps are included with the grip.

12. The surgical instrument of claim 1, wherein the implant comprises a cage.

13. The surgical instrument of claim 12, wherein the cage includes a top shell, a bottom shell, and a joining device.

14. The surgical instrument of claim 13, wherein the grip is connected via the pre-set breaking point to the top shell, the bottom shell, or both the top shell and bottom shell.

15. The surgical instrument of claim 1, wherein a support area or surface at an end of the joining profile includes a guidance groove.

16. The surgical instrument of claim 15, wherein the support area or surface is configured for attachment at a joining profile impact surface or a grip impact surface.

17. The surgical instrument of claim 1, including a template, the template configured for positioning bores in which the joining profile can be inserted or configured for insertion of drills.

18. The surgical instrument of claim 1, including a template configured to support at least one guiding groove for guiding the joining profile with the insertion of the joining profile.

19. A surgical instrument comprising:
an implant including a joining profile including a first leg, a second leg, and a web, the first leg is connected to the web forming a first elbow with about a right angle between the first leg and the web, and the second leg is connected to the web with a second elbow with about a right angle between the second leg and the web;
a grip including a recess formed between the implant and the grip; and
wherein the grip includes a first recess and a second recess, wherein the second recess forms a first pre-set breaking point and a second pre-set breaking point, the first pre-set breaking point connects a first portion of the grip to a first corner of the first elbow providing a connection point between the web and the first leg of joining profile in a depression of the joining profile, and the second pre-set breaking point connects a second portion of the grip to a second corner of the second elbow providing a connection point between the web and the second leg of the joining profile in the depression of the joining profile, and
wherein the recess forms the first and second pre-set breaking points.

20. The surgical instrument of claim 19, wherein the grip further includes at least one template bore.

21. The surgical instrument of claim 19, wherein the recess of the grip is substantially rectangular in shape.

22. A surgical instrument comprising:
an implant comprising a joining profile configured to engage a portion of a bone, the joining profile including a first leg, a second leg, and a web, wherein the first leg is connected to the web forming a first elbow and the second leg is connected to the web forming an second elbow, and the second elbow forms an angle of about 26 degrees between the second leg and the web; and
a grip comprising a first recess and a second recess, wherein the second recess forms a first pre-set breaking point and a second pre-set breaking point;
wherein the first pre-set breaking point connects a first portion of the grip to a first corner of the first elbow providing a connection point between the web and the first leg of the joining profile in a depression of the joining profile; and
the second pre-set breaking point connects a second portion of the grip to a second corner of the second elbow providing a connection point between the web and the second leg of the joining profile in the depression of the joining profile.

* * * * *